(12) United States Patent
Sun

(10) Patent No.: US 7,030,273 B1
(45) Date of Patent: Apr. 18, 2006

(54) COMPOUNDS WITH PHYSIOLOGICAL COOLING EFFECT

(75) Inventor: Hong Sun Sun, Baytown, TX (US)

(73) Assignee: Qaroma, Inc, Baytown, TX (US)

( * ) Notice: Subject to any disclaimer, the term of this patent is extended or adjusted under 35 U.S.C. 154(b) by 0 days.

(21) Appl. No.: 11/079,506

(22) Filed: Mar. 14, 2005

(51) Int. Cl.
*C07C 233/05* (2006.01)

(52) U.S. Cl. ........................ 564/215; 564/224

(58) Field of Classification Search ........... 564/215, 564/224
See application file for complete search history.

(56) References Cited

FOREIGN PATENT DOCUMENTS

GB        1421744      *   6/1976

* cited by examiner

*Primary Examiner*—Shailendra Kumar

(57) ABSTRACT

Novel compounds of 2,3-dimethyl-2-isopropylbutyric acid were claimed in this patent to possess pronounced cooling effect on the skin and on the mucous membranes of the body. These compounds also possess good taste quality and low melting points with no malodor. The preparations and some illustrative application of these compounds are also disclosed.

2 Claims, No Drawings

COMPOUNDS WITH PHYSIOLOGICAL COOLING EFFECT

BACKGROUND OF THE INVENTION

This invention relates to compounds having a physiological cooling effect on the skin and on the mucous membranes of the body, particularly those of the mouth, nose and throat.

Menthol exists abundantly in nature and has been known for a long time as a physiological cooling compound. It is well established that the "cooling" effect of menthol is a physiological effect due to the direct action of menthol on the nerve ends of the human body responsible for the detection of hot or cold and is not due to latent heat of evaporation or dissolution. Menthol has been used widely in cigarettes, cosmetics, toothpastes, chewing gum, sweets, and medicines. Disadvantages of menthol include its strong "stinging" smell, bitter taste, burning sensation in high concentration and high volatility. These undesirable properties limit applications of menthol to some extent.

Since 1960's, researchers have been working on discovering synthetic substitutes of menthol, which possess low volatility and have almost no odor or taste.

The easiest and most straightforward direct modification of l-menthol is to make menthyl esters, such as, menthyl acetate, menthyl lactate (German Patent 2,608,226), saccharide ester of menthol (Swiss Patent 484,032), menthyl 2-hydroxybutyrate (French Patent 2,577,922), menthyl monomenthyl succinate (U.S. Pat. No. 3,111,127), monomenthyl glutarate (U.S. Pat. No. 6,365,215), menthyl hydroxyethyl carbonate (U.S. Pat. No. 3,419,543), etc. Another way to take advantage of hydroxyl group in menthol is to incorporate it to an ether linkage, e.g., menthyl glyceryl ether (U.S. Pat. No. 4,459,425). Ketals of menthone, such as, menthone glycerin ketal can be made readily and it is proven to be a coolant (German Patent 4,266,043 and U.S. Pat. No. 5,266,592) because of the paramenthane moiety in the structure. Menthol analogs are equally attractive, such as, isopulegol (U.S. Pat. No. 5,773,410) and paramenthane-3,8-diol (U.S. Pat. No. 5,959,161). Both compounds are obtained by cyclization of citronellal.

A large variety of compounds without paramenthane structure have also been found to possess cooling property, for instance, cyclohexanol derivatives (German Patent 2,317,000), cyclic secondary and tertiary alcohols (GB Patent 1,404,596), alkylmethanols (German Patent 2,439,770), trialkylphospine oxides (German Patent 2,345,156), cyclic and acyclic sulfoxides and sulfones (German Patent 2,334,985 and German Patent 2,336,495) all show cooling effect, but the strength of the cooling effect varies.

Amides, as cooling agents, might be the most important group of compounds. N,N-dimethyl 2-ethylbutanamide and 2,2-deimethylpropanamide (French Patent 1,572,332) were found to possess physiological cooling effect decades ago. Later on, a large number of cyclic amides with 5- to 11-membered rings (GB Patent 1,489,359, GB Patent 1,489,359, German Patent 2,624,504 and U.S. Pat. No. 4,296,093) were identified as cooling agents. Later, menthol derived amides (U.S. Pat. No. 4,150,052) were discovered as coolants by Wilkinson Sword company. Among these amides, N-ethyl menthane-carboxamide (WS-3) was successfully commercialized.

In 1972 Wilkinson Sword also discovered another attractive series of acyclic amides (2,3-dimethyl-2-isopropylbutyramides, GB 1,421,744), which interestingly do not show much similarity in structure to menthol or menthol derivatives. Of all these amides of highly branched, tertiary acyclic carboxylic acids, N,2,3-trimethyl-2-isopropylbutyramide (WS-23) has been successfully commercialized. WS-23 possesses a strong cooling effect and a good taste quality.

A new current trend is searching for convenient liquid sellable forms of cooling agents with little or no solvent. To find eutectic mixtures of existing cooling agents requires cooling compounds with low melting points and even liquid cooling compounds with comparable cooling effect. Primary amides, e.g. WS-23, with high enough molecular weight are normally highly crystalline due to the intermolecular hydrogen bonding in the structure. Introducing functional groups with oxygen atom in either ether linkage or terminal hydroxyls will promote intramolecular hydrogen bonding, thus lowering intermolecular hydrogen bonding and also affecting packing of those molecules. Therefore it lowers the crystallinity of the compounds, resulting in lower melting points.

It is an object of the present invention to provide new compounds with pronounced physiological cooling effect without the disadvantage of strong odors and bitter taste.

It is also a further object of this invention to provide compounds with pronounced physiological cooling effect and relatively low melting points to provide the possibility of liquid coolants or coolant mixtures.

BRIEF DESCRIPTION OF THE INVENTION

We claim here that a series of compounds with the following structure having strong cooling effect, low melting point but no odor or taste.

The present invention provides a novel series of derivatives of 2,3-dimethyl-2-isopropylbutyric acid, with pronounced physiological cooling effect but no odor or taste. These compounds also possess relatively low melting points. These compounds are of the formula:

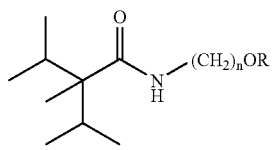

n = 2, R = H, Me, Et
n = 3, R = H, Me, Et, Pr$^i$, Bu

When n equals to 2, R is H or an aliphatic group attached to the oxygen atom; when n equals to 3, R is H or an aliphatic group.

The aliphatic group is intended to include any straight chain or branched alkyl group containing up to 6 carbon atoms. Typical such groups are methyl, ethyl, propyl, isopropyl, butyl, sec-butyl, tert-butyl, etc.

The incorporation of the oxygen atom into the chain of the amine "softens" the molecules, resulting in significantly lower melting points without affecting the taste quality of these compounds.

DETAILED DESCRIPTION OF THE INVENTION

Amides with this formula can be easily prepared by amidation reaction between alkoxyalkylamine (or hydroxyalkylamine) and 2,3-dimethyl-2-isopropylbutyryl chloride in the presence of a hydrogen chloride acceptor as shown in the following scheme. The hydrogen chloride acceptor can be a base, such as, sodium hydroxide, potassium hydroxide, etc, or a tertiary amine, such as, triethylamine, pyridine, etc. Such reactions are entirely conventional and can be understood by persons skilled in the art.

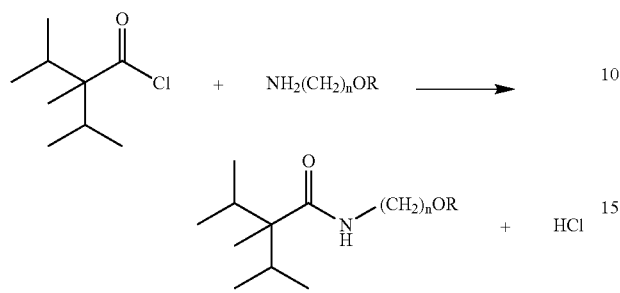

Preparations:

EXAMPLE 1 Preparation of N-(2-hydroxyethyl)-2,3-dimethyl-2-isopropylbutyramide (1)

A mixture of 19.5 g 2-aminoethanol and 50 mL anhydrous hexanes was cooled to 0° C. Under mechanical stirring 20 g freshly distilled 2,3-dimethyl-2-isopropylbutyryl chloride was added dropwise over a period of one hour while maintaining the reaction temperature below 5° C. The reaction mixture was then stirred for one more hour at this temperature followed by one hour at room temperature.

50 mL water was added and the top organic layer was separated and washed with water till is neutral. The solvent was evaporated and 21.5 g crude product (99+% GC purity) was obtained. The product was recrystallized from acetone/water.

EXAMPLE 2 Preparation of N-(3-hydroxypropyl)-2,3-dimethyl-2-isopropylbutyramide (4)

The procedure of Example 1 was repeated using 3-aminopropyl in place of 2-aminoethanol. N-(3-hydroxypropyl)-2,3-diemthyl-2-isopropylbutyramide (4, 99+% GC purity) was obtained as very viscous oil.

EXAMPLE 3 Preparation of N-(2-methoxyethyl)-2,3-isopropylbutyramide (2)

A mixture of 7.74 g 2-methoxyethylamine, 10.95 g triethylamine and 50 mL anhydrous hexanes was cooled to below 5° C. and under mechanical agitation 20 g freshly distilled 2,3-dimethyl-2-isopropylbutyryl chloride was added dropwise over a period of 30 minutes while maintaining the reaction temperature below 25 ° C. After addition the reaction mixture was stirred for 30 minutes at this temperature followed by one hour at room temperature.

50 mL water was added, the top organic layer was separated and washed with 20 mL 5% NaOH solution followed by water till it was neutral. The solvent was evaporated and 24.2 g crude product (2. 98.5+% GC purity) was obtained as viscous oil.

EXAMPLE 4 Preparation of N-(2-ethoxyethyl)-2,3-dimethyl-2-isopropylbutyramide (3)

The procedure of Example 3 was repeated using 2-ethoxyethylamine, in place of 2-methoxyethylamine. N-(2-ethoxyethyl)-2,3-dimethyl-2-isopropylbutyramide (3, 99+% GC purity) was obtained as viscous oil in quantitative yield.

EXAMPLE 5 Preparation of N-(3-methoxypropyl)-2,3-dimethyl-2-isopropylbutyramide (5)

The procedure of Example 3 was repeated using 3-methoxypropylamine in place of 2-methoxyethylamine. N-(3-methoxypropyl)-2,3-dimethyl-2-isopropylbutyramide (5, 99+% GC purity) was obtained in quantitative yield. The crude product was recrystallized with hexanes. m.p. 10° C.

EXAMPLE 6 Preparation of N-(3-ethoxypropyl)-2,3-dimethyl-2-isopropylbutyramide (6)

The procedure of Example 3 was repeated using 3-ethoxypropylamine in place of 2-methoxyethylamine. N-(3-ethoxypropyl)-2,3-dimethyl-2-isopropylbutyramide (6, 99+% GC purity) was obtained in almost quantitative yield. The crude product was recrystallized from acetone/water mixture. m.p. 30° C.

EXAMPLE 7 Preparation of N-(3-isopropoxypropyl)-2,3-dimethyl-2-isopropylbutyramide (7)

The procedure of Example 3 was repeated using 3-isopropoxypropylamine in place of 2-methoxyethylamine. N-(3-isopropoxypropyl)-2,3-dimethyl-2-isopropylbutyramide (7, 99+% GC purity) was obtained in almost quantitative yield. The product was further recrysallized from acetone/water mixture. m.p. 32° C.

EXAMPLE 6 Preparation of N-(3-butoxypropyl)-2,3-dimethyl-2-isopropylbutyramide (8)

The procedure of Example 3 was repeated using 3-butoxypropylamine in place of 2-methoxyethylamine. N-(3-butoxypropyl)-2,3-dimethyl-2-isopropylbutyramide (8, 99+% GC purity) was obtained in almost quantitative yield. The product was further purified by recrystallization from acetone/water mixture. m.p. 40° C.

Evaluation procedure:

The following testing procedure is aimed at determining physiological cooling ability of testing compounds with regard to WS-23 (N,2,3-Dimethyl-2-isopropylbutyramide). The tests are carried out on a selected panel of 5 people. The present test procedure is done on a statistical basis because sensitivity to cooling compounds will vary not only from compound to compound and from one part of the body to another, but from one individual to another as well. Tests of this nature are commonly used on the testing and quality control of the organoleptic properties, e.g. taste, smell of organic and inorganic food products.

1 g of each testing compound is dissolved in 99 g denatured ethanol to form 1% solution. 2 g such solution is then diluted with 8 g deionized water to form 2000 ppm solution. The solutions are then applied orally to determine the cooling effect.

To test the cooling activity of the compounds in this invention, the compounds prepared in this invention are tested repeatedly by the 5 selected panelists and the results are compared with WS-23.

These compounds all have a pronounced physiological cooling ability, and 1 mL 2000 ppm solution provides cooling sensation that lasts for 30 minutes. Several compounds exhibit equal or stronger cooling ability than WS-23.

The results are summarized in the table below.

| Entry | Compounds | m.p. | Cooling ability compared to WS-23 |
|---|---|---|---|
| 1 | 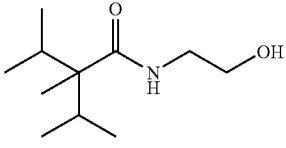 | 28° C. | − |
| 2 | 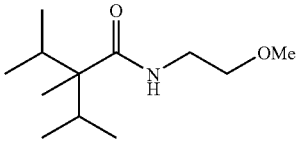 | − | − |
| 3 | 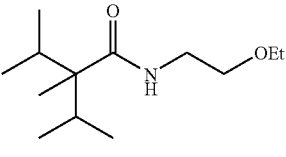 | | + |
| 4 | 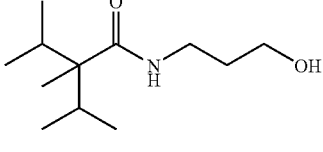 | | − |
| 5 | 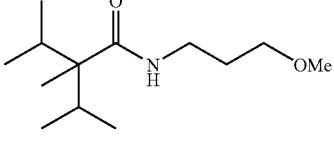 | 10° C. | + |
| 6 | 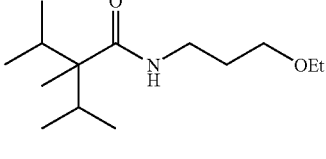 | 30° C. | + |
| 7 | 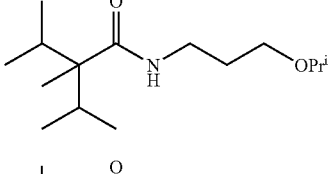 | 32° C. | + |
| 8 | 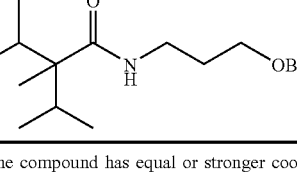 | 40° C. | + |

+ means the compound has equal or stronger cooling effect than WS-23.

APPLICATIONS

The compounds in this invention give a physiological cooling effect on cold receptors of the skin and mucous membranes of the human body, especially those in the mouth, nose and throat. They can find a wide variety of applications in consumer products for consumption by or application to the human body. They can be added in candies and drinks to give cooling feeling. They can be incorporated toothpaste and other oral hygiene products to provide the long-lasting cooling, refreshing sensation. They can also be applied in medicines, such as in ointment and cough drops to provide soothing effect to relieve the burning on the skin and irritations to the throat.

Following are some examples utilizing compounds in this invention as physiological cooling agents. The applications of these compounds will not be limited to these examples.

Toothpicks:

Toothpick tips were soaked in 5% solution of Compound 3 in this invention in denatured ethanol for long enough to have enough deposition of the compound. The picks were then dried. When put on tongue, only pronounced cooling sensation exhibited with no detectable taste.

Mint candies:

Icing sugar was mixed with small amount of water at 50° C. to form a paste. 0.02% Compound 5 in this invention was added and stirred. Cooled to room temperature, the mixture hardened and was broken into smaller pieces. The candies had a marked cooling effect in the mouth.

| Toothpaste: | |
|---|---|
| Compound 6 in this invention | 0.2% |
| Saccharine | 0.2% |
| Flavor | 0.8% |
| Potassium hydrophosphate (buffer) | 40% |
| Carboxymethyl cellulose | 1.0% |
| Synthetic sodium lauryl sulfate | 2.0% |
| Gel | 25.0% |
| Deionized water | to 100% |

Toothpaste prepared this way gives refreshing sensation.

| Mouthwash: | |
|---|---|
| Menthol | 1.0% |
| Compound 7 in this invention | 0.5% |
| Sodium saccharine | 0.3% |
| Denatured ethanol | 40.0% |
| PEG hydrogenated castor oil | 0.5% |
| Deionized water | to 100% |

Using the mouthwash prepared according to this recipe gives clean, crispy breath without giving the bitter taste.

We claim:

1. N-alkoxyalkyl substituted-2,3-dimethyl-2-isopropyl-butyramides of the formula shown below as new compounds with physiological cooling effect,

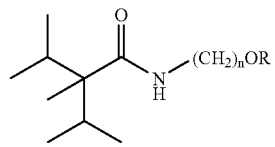

wherein R is C1—C6 alkyl, and n equals 2 or 3.

2. Amides according to claim 1 as cooling agents with low melting points.

* * * * *

UNITED STATES PATENT AND TRADEMARK OFFICE
CERTIFICATE OF CORRECTION

PATENT NO. : 7, 030, 273 B1  Page 1 of 1
APPLICATION NO. : 11/079506
DATED : April 18, 2006
INVENTOR(S) : Hong Sun It is certified that error appears in the above-identified patent and that said Letters Patent is hereby corrected as shown below:

Title Page # 75 Should read
Inventor: Hong Sun

Signed and Sealed this

Eighth Day of August, 2006

JON W. DUDAS
*Director of the United States Patent and Trademark Office*